United States Patent
Simpson et al.

(10) Patent No.: US 9,848,919 B2
(45) Date of Patent: Dec. 26, 2017

(54) SPINAL CONSTRUCT AND METHODS OF USE

(71) Applicant: Warsaw Orthopedic, Inc., Warsaw, IN (US)

(72) Inventors: Joshua W. Simpson, Collierville, TN (US); Dennis G. Crandall, Mesa, AZ (US); Richard Quinn Brown, Collierville, TN (US); Matthew Van Nortwick, Kalamazoo, MI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 85 days.

(21) Appl. No.: 14/704,156

(22) Filed: May 5, 2015

(65) Prior Publication Data
US 2016/0324546 A1 Nov. 10, 2016

(51) Int. Cl.
*A61B 17/70* (2006.01)

(52) U.S. Cl.
CPC ...... *A61B 17/7053* (2013.01); *A61B 17/7001* (2013.01); *Y10S 411/999* (2013.01)

(58) Field of Classification Search
CPC .................. A61B 17/7053; A61B 17/7001
See application file for complete search history.

(56) References Cited

U.S. PATENT DOCUMENTS

| | | | | |
|---|---|---|---|---|
| 2,389,344 A * | 11/1945 | Constance | ................ | F16B 5/10 411/105 |
| 2,715,216 A * | 8/1955 | Howenstine | ....... | H01R 33/0845 174/153 R |
| 3,578,799 A * | 5/1971 | Davis | ....................... | B23Q 3/06 269/296 |
| 5,228,875 A * | 7/1993 | Swenson, Sr. | ......... | H01R 4/308 174/84 S |
| 5,573,537 A * | 11/1996 | Rogozinski | ........ | A61B 17/1671 408/225 |
| 6,056,753 A * | 5/2000 | Jackson | ............. | A61B 17/7032 411/5 |
| 6,695,653 B1 * | 2/2004 | Tomasino | ............ | H01R 4/5033 439/428 |
| 6,783,527 B2 * | 8/2004 | Drewry | .............. | A61B 17/7031 606/254 |
| 7,901,233 B2 * | 3/2011 | Melni | ...................... | H01R 4/56 439/271 |
| 8,066,525 B2 * | 11/2011 | Melni | ...................... | H01R 4/56 439/271 |
| 8,292,958 B1 * | 10/2012 | Bruffey | ................... | A61F 2/442 606/246 |
| 8,328,849 B2 * | 12/2012 | Nydegger | .......... | A61B 17/7022 606/254 |
| 2009/0264930 A1 * | 10/2009 | McBride | ............ | A61B 17/7004 606/250 |
| 2013/0072983 A1 * | 3/2013 | Lindquist | ........... | A61B 17/7049 606/278 |
| 2014/0148854 A1 * | 5/2014 | Carlson | ............. | A61B 17/7049 606/254 |

(Continued)

*Primary Examiner* — Ellen C Hammond
*Assistant Examiner* — Stuart S Bray (57) ABSTRACT

A spinal construct comprising a first portion. A second portion defines a longitudinal axis and is configured to penetrate tissue. A tether is fastened with the first portion such that a spinal implant connected with the tether is movable to a plurality of orientations relative to the longitudinal axis. Systems and methods are disclosed.

18 Claims, 9 Drawing Sheets

(56) References Cited

U.S. PATENT DOCUMENTS

| | | | |
|---|---|---|---|
| 2014/0296918 A1* | 10/2014 | Fening | A61B 17/7016 606/258 |
| 2015/0164561 A1* | 6/2015 | Simpson | A61B 17/7002 606/264 |
| 2015/0201973 A1* | 7/2015 | Lindemann | A61B 17/7022 606/263 |
| 2016/0324547 A1* | 11/2016 | Miller | A61B 17/7001 |

\* cited by examiner

SPINAL CONSTRUCT AND METHODS OF USE

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ spinal constructs including implants such as rods, tethers and bone screws for stabilization of a treated section of a spine. This disclosure describes an improvement over these prior art technologies.

SUMMARY

In one embodiment, a spinal construct is provided. The spinal construct comprises a first portion. A second portion defines a longitudinal axis and is configured to penetrate tissue. A tether is fastened with the first portion such that a spinal implant connected with the tether is movable to a plurality of orientations relative to the longitudinal axis. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a spinal implant system and related methods of use disclosed are discussed in terms of medical devices for the treatment of musculoskeletal disorders and more particularly, in terms of a spinal implant system and a method for correction of a spine disorder. In some embodiments, the spinal implant system includes a spinal construct including an implant, such as, for example, a bone fastener connected with a tether. In some embodiments, the bone fastener may include a screw, post and/or a connector.

In some embodiments, the spinal implant system includes a spinal construct comprising a tether attached to a pedicle screw. In some embodiments, the spinal implant system is employed with a method for attaching the tether with the pedicle screw. In some embodiments, the spinal implant system is employed with a method for reducing a spinal rod to a spine. In some embodiments, the spinal implant system is employed with a method comprising one or a plurality of correction techniques.

In some embodiments, the spinal implant system includes a spinal construct comprising a tether inserted with a top of a screw and swaged to the top of the screw. In some embodiments, the spinal implant system includes a spinal construct comprising a tether inserted with a top of a screw and the tether is pinned to the top of the screw through the body of the screw. In some embodiments, the spinal implant system includes a spinal construct comprising a tether inserted with a top of a screw and the top of the screw includes a threaded collet. In some embodiments, a nut passes over the top of the screw and closes the collet down onto the tether.

In some embodiments, the spinal implant system includes a spinal construct comprising a bone fastener including a cavity configured to receive a tether. In one embodiment, a wall of the cavity is swaged to the tether to resist and/or prevent the tether from disengaging and/or pulling out from the bone fastener. In some embodiments, the bone fastener includes an external hex drive. In some embodiments, the spinal implant system includes a spinal construct comprising a tether disposed with a cavity of the bone fastener and a pin is utilized to connect the tether with the bone fastener. In some embodiments, the bone fastener includes a collet configured to connect the tether with the bone fastener. In some embodiments, the tether is inserted into the bone fastener and a nut is disposed over the collet to fix the collet with the tether. In one embodiment, the nut is laser welded to the collet. In some embodiments, the bone fastener is connected with the tether for form a multi planar adjusting spinal construct. In one embodiment, the spinal implant system includes a spinal construct configured for attachment from a posterior surgical approach to a spine.

In one embodiment, the spinal implant system includes a spinal construct comprising a tether and a connector, which can be employed, for example, with a method for treating proximal junction kyphosis (PJK). In one embodiment, the spinal implant system includes a spinal construct comprising a tether having a loop. In some embodiments, the loop includes a metal insert. In one embodiment, the spinal implant system includes a spinal construct comprising a connector having a slot configured for disposal of the tether. In one embodiment, the spinal implant system includes a spinal construct comprising a crown configured to compress, engage and/or penetrate the tether. In one embodiment, the crown grips the tether. In one embodiment, the spinal implant system includes a setscrew, a spinal rod, a crown and a tether. In one embodiment, the tether is pulled through the connector to tighten the spinal rod.

In some embodiments, the spinal implant system includes a spinal construct comprising a bone fastener having a threaded post, a suture, such as, for example, mersilene tape and a connector to top off the construct, and can be employed with a method to treat PJK. In some embodiments, the spinal implant system includes a spinal construct comprising a posted bone screw, a tether and a set screw configured to connect the tether with the screw. In one embodiment, the tether has a grommet configured for disposal about the posted screw.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
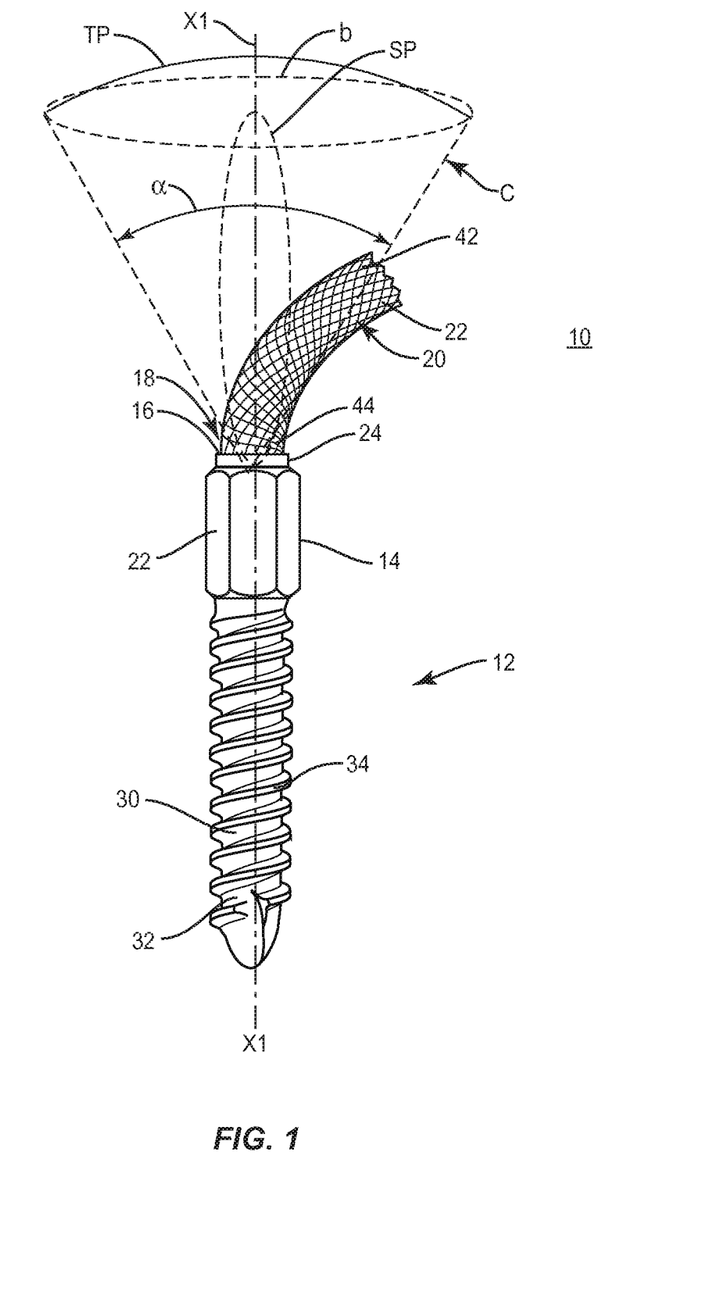
FIG. 1 is a side view of components of one embodiment of a spinal implant system in accordance with the principles of the present disclosure.
Figure 2:
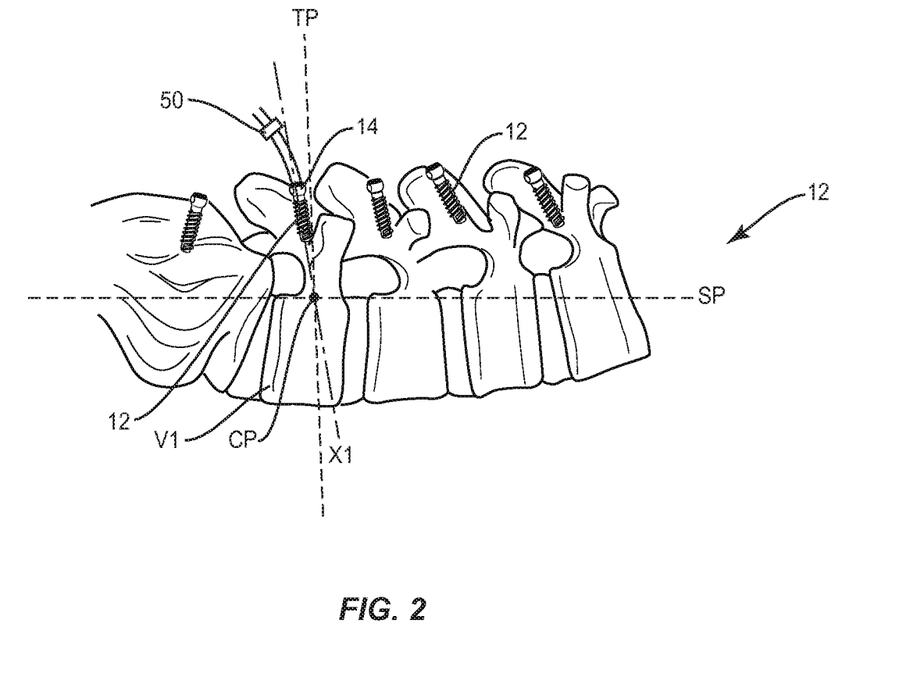
FIG. 2 is a side view of components of one embodiment of a spinal implant system in accordance with the principles of the present disclosure disposed with vertebrae.

The following discussion includes a description of a spinal implant system including a spinal construct, related components and methods of employing the spinal implant system in accordance with the principles of the present disclosure. Alternate embodiments are also disclosed. Reference is made in detail to the exemplary embodiments of the present disclosure, which are illustrated in the accompanying figures. Turning to FIGS. 1-2, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TOP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening dements and/or instruments, as described herein.

Spinal implant system 10 includes a bone fastener, such as, for example, a posted pedicle screw 12. Screw 12 includes a portion, such as, for example, a post 14. Post 14 includes a surface 16 that defines a cavity 18. Cavity 18 is configured for disposal of at least a portion of a longitudinal element, such as, for example, a tether 20, as described herein. In some embodiments, cavity 18 may have alternate cross section configurations, such as, for example, oval, oblong triangular, square, polygonal, irregular, uniform, non-uniform, offset, staggered, and/or tapered. In some embodiments, cavity 18 may be disposed at alternate orientations, relative to a portion, such as, for example, a shaft 30, described herein, such as, for example, transverse, perpendicular and/or other angular orientations such as acute or obtuse, coaxial and/or may be offset or staggered. In some embodiments, surface 16 may include alternate fixation configurations, such as, for example, friction fit, pressure fit, locking protrusion/recess, locking keyway and/or adhesive to facilitate connection of tether 20 with post 14.

Post 14 includes an outer surface 22. In one embodiment, surface 22 is configured for engagement with an insertion tool, compression instrument and/or other instruments to facilitate manipulation and/or fastening of bone fastener 12 with tissue and/or connection of tether 20 with cavity 18. In one embodiment, surface 22 includes a hexalobe geometry configured for engagement with a similarly shaped tool, such as, for example, a driver. In some embodiments, surface 22 has a cruciform, phillips, square, hexagonal, polygonal, star or hexalobe cross sectional configuration for disposal of a correspondingly shaped portion of a driver. In some embodiments, all or only a portion of post 14 may have alternate cross section configurations, such as, for example, oval, oblong, triangular, square, polygonal, irregular, uniform, non-uniform, offset, staggered, and/or tapered. Surface 16 and surface 22 define a wall 24. Wall 24 is circumferentially disposed about cavity 18. Wall 24 is engageable with the surface of tether 20 to fix tether 20 with post 14.

In one embodiment, wall 24 is deformable and/or malleable, such as, for example, via swaging, hammering, compressing and/or crimping, such that wall 24 engages tether 20 in a, for example, friction fit, pressure fit, compression and/or penetration to fix tether 20 with post 14. In some embodiments, wall 24 and/or the surface of tether 20 includes adhesive material to facilitate fixation of wall 24 with tether 20.

Shaft 30 includes an end 32, as shown in FIG. 1, configured to penetrate tissue, such as, for example, bone. Shaft 30 defines an axis X1. In one embodiment, end 32 includes a threaded surface 34. Tether 20 is configured for connection with post 14 such that a spinal implant, such as, for example, a connector 50 is moveable to a plurality of orientations relative to axis X1. In one embodiment, the spinal implant includes a spinal rod connected with tether 20 and is moveable to a plurality of orientations relative to axis X1.

Tether 20 is a flexible longitudinal element that extends between an end 42 and an end 44. End 44 is configured for insertion into cavity 18 and engagement with wall 24, as described herein. In some embodiments, a portion of tether 20 forms a loop configured to surround all or a portion of tissue, such as, for example, laminae and/or a spinal implant, such as, for example, a connector or a spinal rod, as described herein. In some embodiments, tether 20 is configured for tensioning about a targeted portion of an anatomy of a body for attachment of tether 20 with the targeted portion of the anatomy, as described herein. In some embodiments, the targeted portion of the anatomy may include laminae, transverse process and/or pedicle regions of a vertebral level. In some embodiments, spinal implant system 10 may include one or a plurality of tethers 20, each tether being configured for disposal about a single and separate vertebral level. In some embodiments, a single vertebral level may include one or a plurality of tethers 20. In some embodiments, a single tether 20 may be disposed about a plurality of vertebral levels.

Tether 20 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 20 includes movement in a lateral or side to side direction and prevents expanding and/or extension in an axial direction upon tensioning and attachment with a targeted portion of the anatomy. In some embodiments, all or only a portion of tether 20 may have a semi-rigid, rigid or elastic configuration, and/or have elastic properties, similar to the material examples described above, such that tether 20 provides a selective amount of expansion and/or extension in an axial direction. In some embodiments, tether 20 may be compressible in an axial direction. Tether 20 can include a plurality of separately attachable or connectable portions or sections, such as bands or loops, or may be monolithically formed as a single continuous element.

Tether 20 can have a uniform thickness/diameter. In some embodiments, tether 20 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 20 may be uniformly increasing or decreasing, or have alternate diameter dimensions along its length. In some embodiments, tether 20 may have various cross section configurations, such as, for example, oval, oblong, triangular, rectangular, square, polygonal, irregular, uniform, non-uniform, variable and/or tapered. In some embodiments, the surface of tether 20 may include engaging structures, such as, for example, barbs, raised elements and/or spikes to facilitate engagement with tissue of the targeted anatomy.

In some embodiments, tether 20 may have various lengths. In some embodiments, tether 20 may be braided, such as a rope, or include a plurality of elongated elements to provide a predetermined force resistance. In some embodiments, tether 20 may be made from autograft and/or allograft, and be configured for resorbable or degradable applications. In one embodiment, tether 20 is a cadaver tendon. In one embodiment, tether 20 is a tendon that may be harvested, for example, from a patient or donor. In some embodiments, a tendon harvested from a patient may be affixed in remote locations with the patient's body.

In some embodiments, tether 20 is mechanically coupled, such as, for example, by swaging post 14 with tether 20. In some embodiments, wall 24 is engaged with a swage device, anvil and/or one or more dies to deform wall 24 such that surface 16 engages, compresses and/or penetrates the surface of tether 20 to fix post 14 with tether 20. In some embodiments, the swaging operation for deformation of wall 24 may include extrusion or radial forging. In some embodiments, tether 20 is mechanically coupled to post 14 via squeezing wall 24 with pliers, hammering wall 24 with a mallet to deform wall 24, and/or adhering the surface of tether 20 to surface 16 with an adhesive.

Connector 50 is connected with tether 20 and is movable relative to axis X1 to a plurality of orientations. In some embodiments, connector 50 is movable relative to axis X1 to a plurality of orientations, such as, for example, a plurality of axes within an angular range of α. In some embodiments, connector 50 is connected with tether 20 and is movable relative to axis X1 to a plurality of orientations, such as, for example, a plurality of planes of a body, such as, for example, sagittal plane SP, coronal plane CP and/or transverse plane TP, as shown in FIGS. 1 and 2.

Tether 20 is rotatable to a selected angle through and within angular range α relative to axis X1 in a plurality of planes that lie in a cone configuration C, as shown in FIG. 1. The area and/or volume defined by cone C, which includes the configuration disposed between axis X1 and a circular base b, is defined by the range of motion of tether 20 about axis X1. The plurality of planes includes a locus of all straight line segments that join axis X1 and base b. For example, tether 20 is separately rotatable to a selected angle within angular range α in each plane corresponding to a particular straight line segment that lies in cone configuration C. In some embodiments, tether 20 may be rotatable through the individual diameters, chords, section and/or radii of base b and/or other portions of cone C. In one embodiment, tether 20 is rotatable to a selected angle within angular range α in sagittal plane SP, corresponding to a particular plane that lies in cone C. In one embodiment, tether 20 is rotatable to a selected angle within angular range α in transverse plane TP, corresponding to a particular plane that lies in cone C. In one embodiment, tether 20 is rotatable to a selected angle within angular range α in coronal plane CP, corresponding to a particular plane that lies in cone C. In some embodiments, tether 20 is rotatable to a selected angle within angular range α of 0 through 360 degrees relative to axis X1.

In assembly, operation and use, spinal implant system 10, similar to the systems and methods described herein, includes pedicle screw 12, described herein, and is employed with a surgical procedure for treatment of a spinal disorder affecting a section of a spine of a patient, as discussed herein. Spinal implant system 10 is employed with a surgical procedure for treatment of a condition or injury of an affected section of the spine. In some embodiments, spinal implant system 10 can be employed with a method for treatment of PJK found in scoliosis patients post-operatively after undergoing scoliosis surgery.

In use, to treat the affected section of the spine, a medical practitioner obtains access to a surgical site in any appropriate manner, such as through incision and retraction of tissues. In some embodiments, the components of spinal implant system 10 may be used in any existing surgical method or technique including open surgery, mini-open surgery, and minimally invasive surgery including percutaneous surgical implantation. Once access to the surgical site(s) is obtained, the particular surgical procedure is performed for treating the spinal disorder. The components of spinal implant system 10 including pedicle screws 12 are employed to augment the surgical treatment. Pedicle screws 12 and one or a plurality of spinal implants, such as, for example, connectors 50 described herein, can be delivered or implanted as a pre-assembled device or can be assembled in situ. Spinal implant system 10 may be may be completely or partially revised, removed or replaced.

In some embodiments, the components of one or more pedicle screws 12 are attached, manufactured and/or assembled, as described herein, prior to implantation. In some embodiments, the components of one or more pedicle screws 12 are attached, manufactured and/or assembled, as described herein, in situ. Wall 24 is connected, as described herein, to the surface of tether 20 to fix tether 20 with post 14.

A driver is engaged with pedicle screw 12. The driver is rotated causing pedicle screw 12 to translate axially within a pilot hole of tissue, such as, for example, vertebrae V, as shown in FIG. 2, such that shaft 30 is threaded and engaged with vertebrae V. In some embodiments, pedicle screw 12 is disposed adjacent vertebrae V at a surgical site and is manipulated to drive, torque, insert or otherwise connect pedicle screw 12 with a single vertebral level V1 of vertebrae V. Connector 50 is connected with tether 20, as shown in FIG. 2, and movable to a plurality of orientations relative to axis X1, as described herein, for positioning and orientation relative to vertebrae V, for example, for alignment and/or capture of a spinal implant, such as, for example, a spinal rod (not shown) and/or attachment with vertebrae V.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, one or more bone fasteners, as described herein, may comprise multi-axial screws, sagittal angulation screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 3:
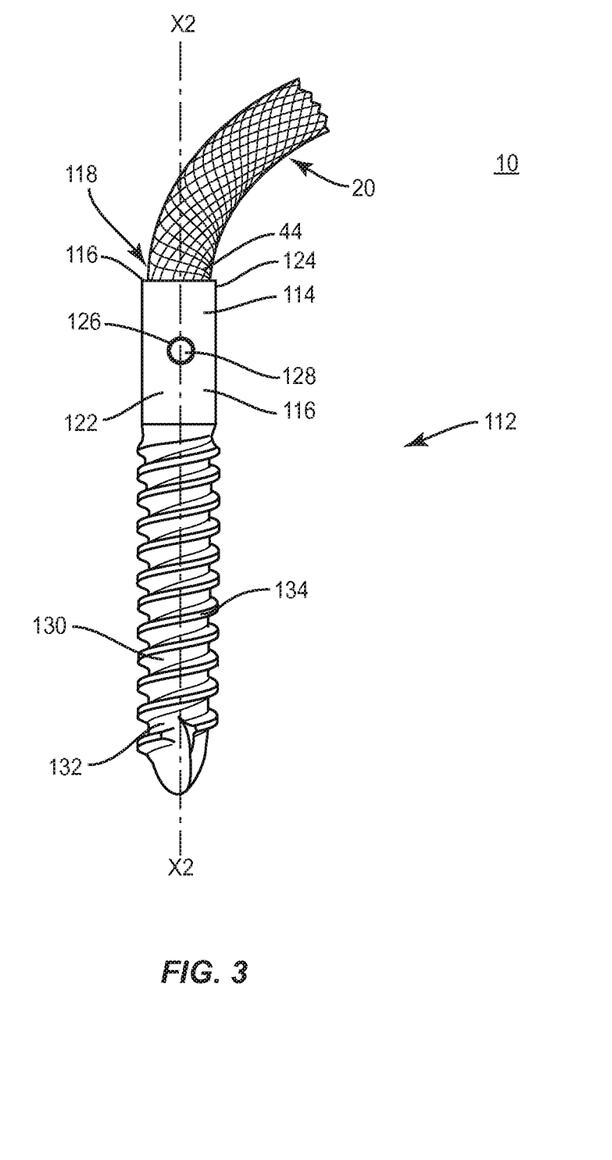
FIG. 3 is a side view of components of one embodiment of a spinal implant system in accordance with the principles of the present disclosure.

In one embodiment, as shown in FIG. 3, spinal implant system 10, similar to the systems and methods described herein, comprises a bone fastener, such as, for example, a bone screw 112, similar to screw 12 described herein. Bone screw 112 includes a post 114. Post 114 includes a surface 116 that defines a cavity 118, similar to surface 16 and cavity 18 described herein. Cavity 118 is configured for disposal of tether 20, as described herein. Post 114 includes an outer surface 122, similar to surface 22 described herein.

Surface 116 and surface 122 define a wall 124. Wall 124 is circumferentially disposed about cavity 118. Surfaces 116, 122 define openings, such as, for example, slots 126 extending through wall 124. Slots 126 are aligned and are configured for disposal of a pin 128. Pin 128 is configured fix tether 20 with post 114. Pin 128 extends between and into slots 126 and penetrates end 44 of tether 20 to fix tether 20 with post 114.

Shaft 130 includes an end 132 configured to penetrate tissue, such as, for example, bone. Shaft 130 defines an axis X2. In one embodiment, end 132 includes a threaded surface 134. Tether 20 is configured for connection with post 114 such that a spinal implant connected with tether 20, as described herein, is moveable to a plurality of orientations relative to axis X2, as described herein.

Figure 4:
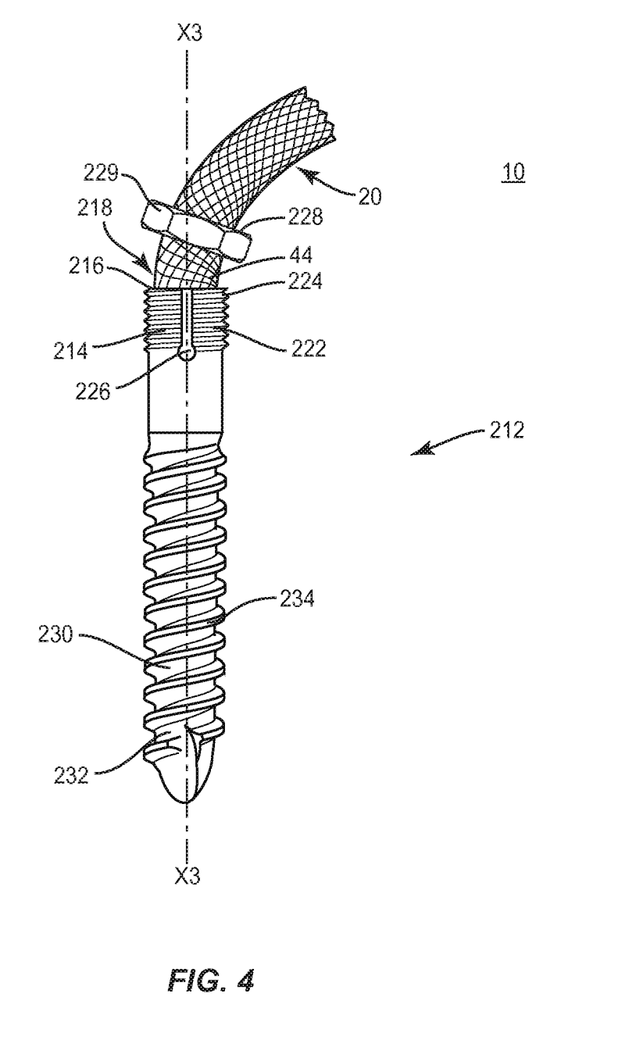
FIG. 4 is a side view of components of one embodiment of a spinal implant system in accordance with the principles of the present disclosure.

In one embodiment, as shown in FIG. 4, spinal implant system 10, similar to the systems and methods described herein, comprises a bone fastener, such as, for example, a bone screw 212, similar to screw 12 described herein. Screw 212 includes a post 214. Post 214 includes a surface 216 that defines a cavity 218, similar to surface 16 and cavity 18 described herein. Cavity 218 is configured for disposal of at least a portion of tether 20, as described herein.

Post 214 includes a threaded outer surface, such as, for example a collet 222. Collet 222 includes a wall 224. Wall 224 is circumferentially disposed about cavity 218. Wall 224 includes spaced sections that define axial openings 226 extending through wall 224. Openings 226 are configured to close upon compression of collet 222 to engage and/or compress tether 20 with wall 224. In some embodiments, the sections of wall 224 are movable between an expanded orientation such that tether 20 is movable relative to post 214 and a contracted orientation such that tether 20 is fixed with post 214. In some embodiments, the sections of wall 224 are biased to the expanded orientation. In some embodiments, the sections of wall 224 are elastic and/or flexible. In some embodiments, the sections of wall 224 are plastically deformable and/or malleable, similar to that described with regard to wall 24.

Collet 222 is engageable with an actuator, such as, for example, a nut 228. Nut 228 includes a threaded surface 229 configured for engagement with collet 222 such that translation of nut 228 over wall 224 causes compression and/or contraction of the sections of wall 224 and closing of openings 226. As such, the sections of wall 224 close about tether 20 to engage tether 20 and fix tether 20 with post 214. Surface 229 is configured to engage collet 222 to facilitate contraction of collet 222, as discussed herein.

Shaft 230 includes an end 232 configured to penetrate tissue, such as, for example, bone. In one embodiment, nut 228 is laser welded to collet 222 to fix tether 20 with post 214. Shaft 230 includes an end 232 configured to penetrate tissue, such as, for example, bone. Shaft 230 defines an axis X3. In one embodiment, end 232 includes a threaded surface 234. Tether 20 is configured for connection with post 214 such that a spinal implant connected with tether 20, as described herein, is moveable to a plurality of orientations relative to axis X3, as described herein.

Figure 5:
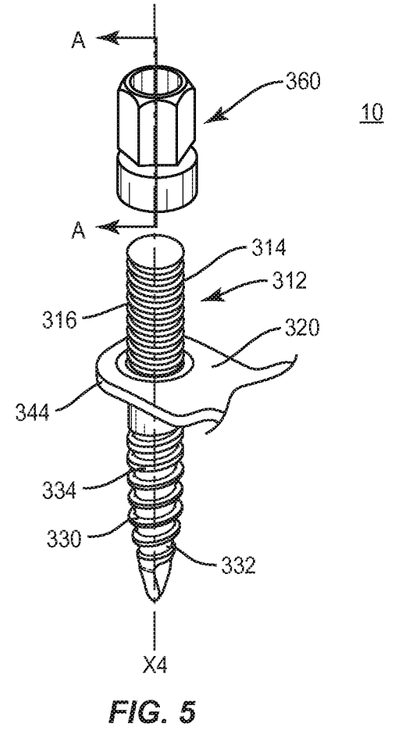
FIG. 5 is a perspective view of components of one embodiment of a spinal implant system in accordance with the principles of the present disclosure with parts separated.
Figure 6:
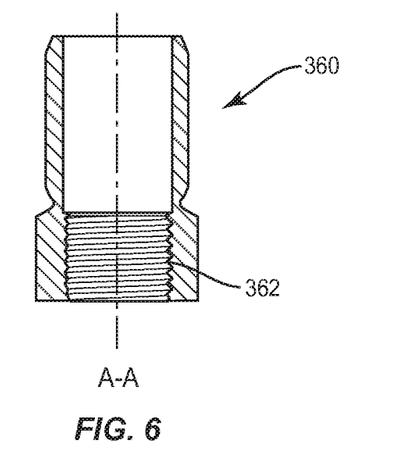
FIG. 6 is a cross section view along line A-A shown in FIG. 5.
Figure 7:
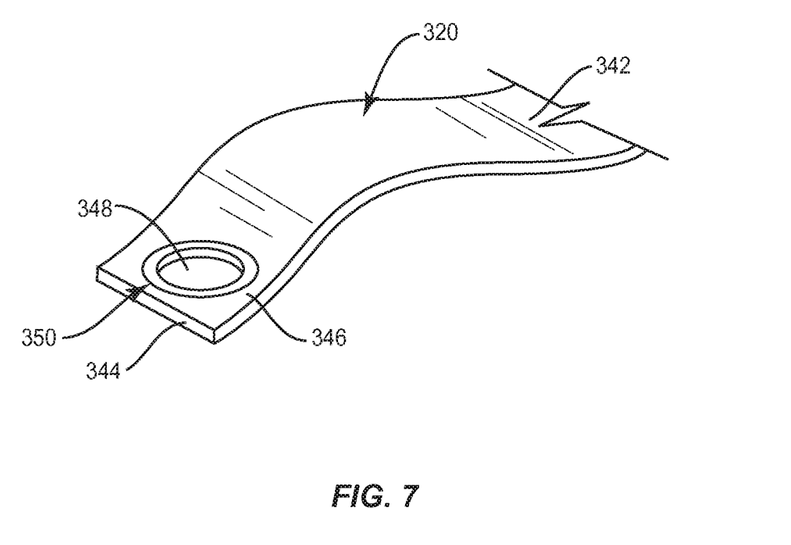
FIG. 7 is a break away view of a component of the system shown in FIG. 5.

In one embodiment, as shown in FIGS. 5-7, spinal implant system 10, similar to the systems and methods described herein, comprises a bone fastener, such as, for example, a bone screw 312. Bone screw 312 includes a threaded post 314 and a shaft 330 having an end 332, as shown in FIG. 5, configured to penetrate tissue, such as, for example, bone. Shaft 330 defines an axis X4. In one embodiment, end 332 includes a threaded surface 334.

Figure 8:
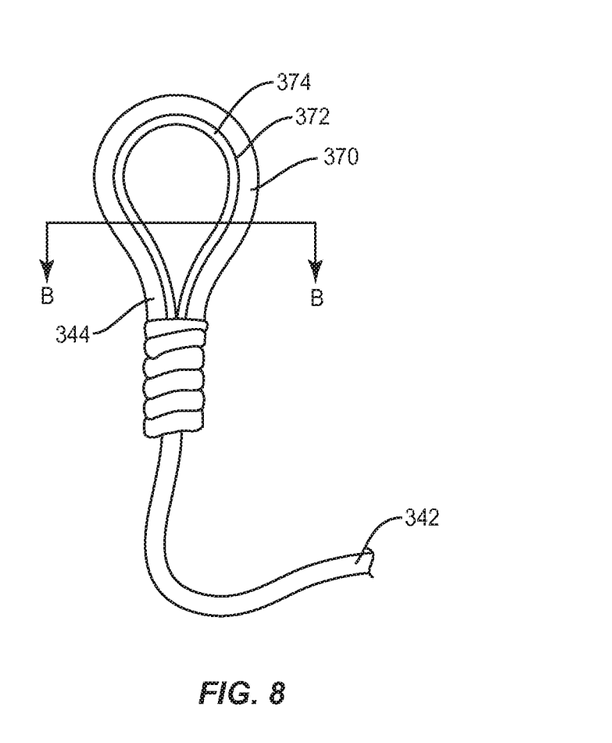
FIG. 8 is a plan view of components of one embodiment of a spinal implant system in accordance with the principles of the present disclosure.
Figure 9:
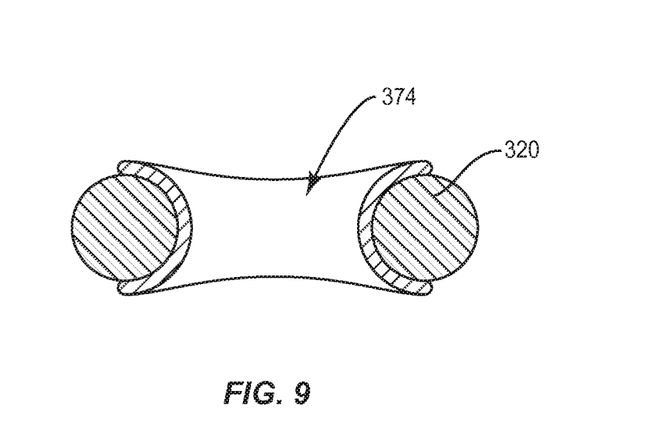
FIG. 9 is a cross section view along line B-B shown in FIG. 8.

A tether 320 is configured for connection with post 314 such that a spinal implant, similar to that described herein, is moveable to a plurality of orientations relative to axis X4, as described herein. Tether 320 extends between an end 342 and an end 344. In one embodiment, as shown in FIG. 7, end 344 is configured for disposal about post 314. End 344 includes a surface 346 that defines an opening 348. Opening 348 includes a grommet 350 disposed about surface 346 to reinforce and strengthen opening 348. In some embodiments, tether 320 includes mersilene tape. In some embodiments, as shown in FIGS. 8 and 9, end 344 forms a loop 370, which includes a metal ring insert 374, configured for disposal about post 314. Loop 370 includes a surface 372 attached with insert 374. Insert 374 is configured to reinforce and strengthen loop 370.

A locking element, such as, for example, a setscrew 360, as shown in FIGS. 5 and 6, includes a threaded surface 362 configured to engage post 314. Setscrew 360 is configured for translation along post 314 to engage grommet 350 (or insert 374) of tether 320. Setscrew 360 is configured to fix tether 320 with post 314 while allowing movement of tether 320 in the plurality of orientations relative to axis X4, as described herein.

In one embodiment, as shown in FIGS. 10-13, spinal implant system 10, similar to the systems and methods described herein, comprises a connector 400 including a body 402 having a surface 404 that defines a cavity, such as, for example, a passageway 406 configured for disposal of tether 20 described herein. Body 402 includes a surface 408 defining a cavity 410 configured for disposal of tether 20. In some embodiments, cavity 410 is disposed in alignment, offset or staggered from passageway 406. In some embodiments, passageway 406 and/or cavity 410 may have various cross section configurations, such as, for example, oval, oblong, triangular, rectangular, square, polygonal, irregular, uniform, non-uniform, variable and/or tapered. In some embodiments, surface 404 and/or surface 408 may include gripping elements or surfaces, such as, for example, rough, arcuate, undulating, mesh, porous, semi-porous, dimpled and/or textured to facilitate engagement with tether 20. Body 402 includes a surface 412 that defines a cavity, such as, for example, an opening 414. Opening 414 is configured for disposal of a locking element, such as, for example, a set screw 416.

Figure 10:
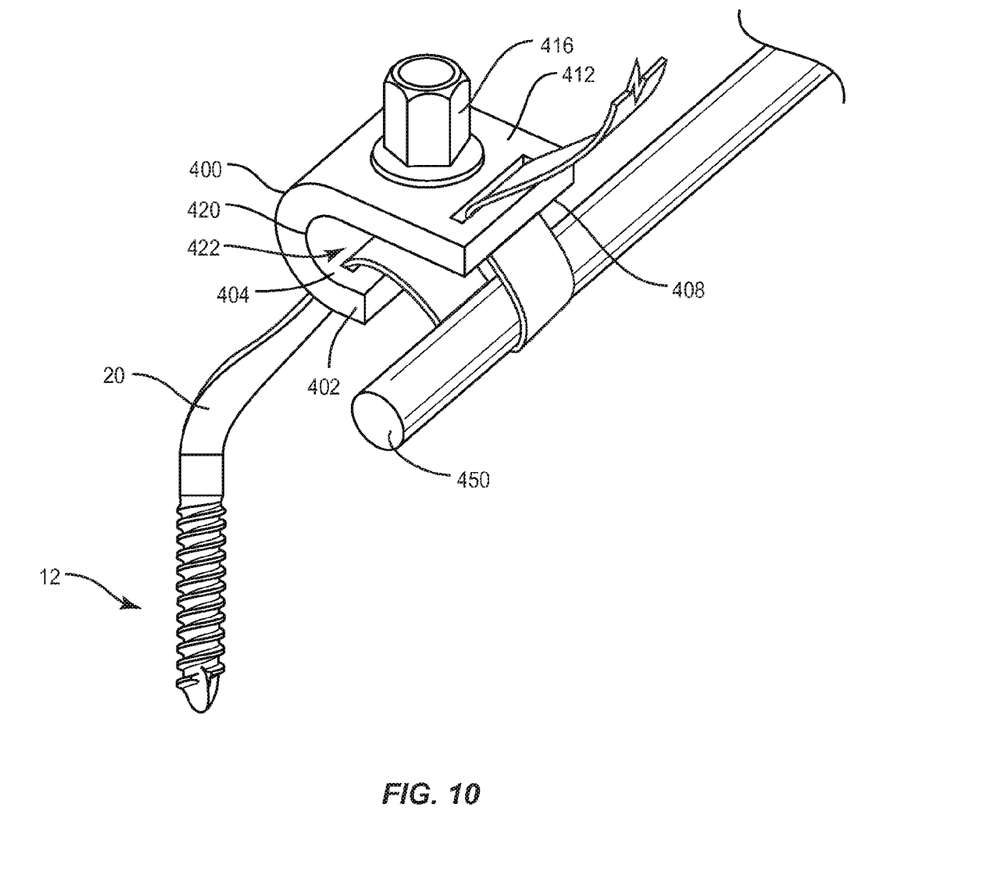
FIG. 10 is a perspective view of components of one embodiment of a spinal implant system in accordance with the principles of the present disclosure.
Figures 11, 12:
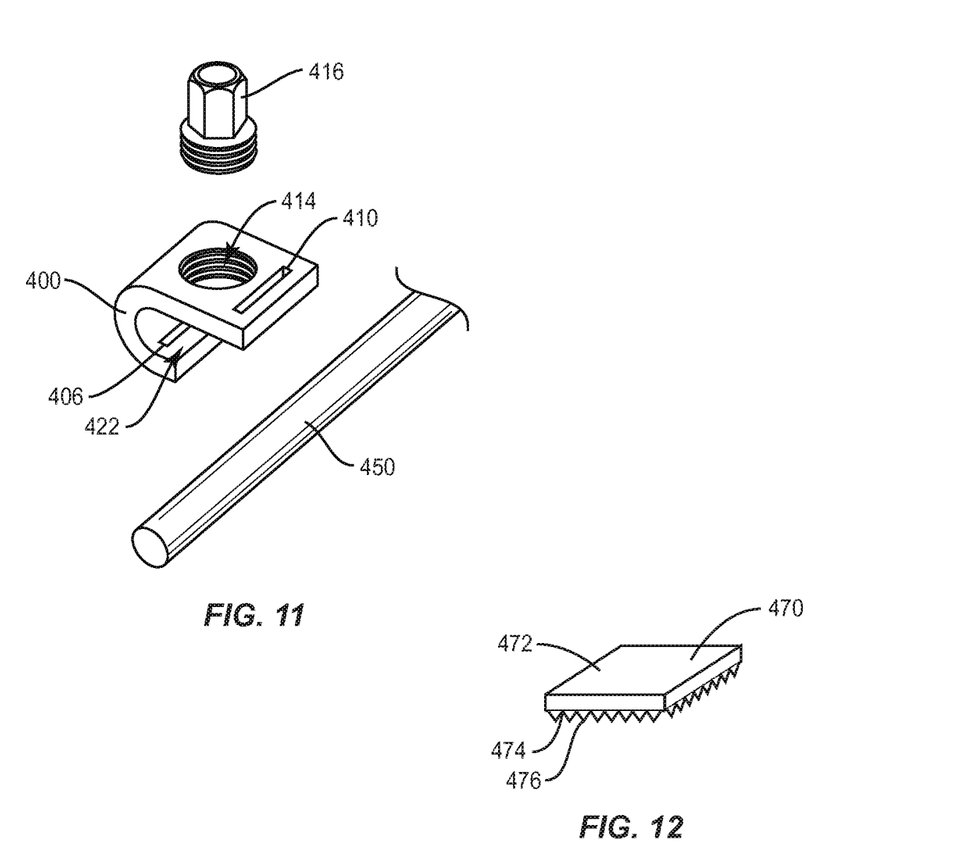
FIG. 11 is a perspective view of components of the system shown in FIG. 10 with parts separated.
FIG. 12 is a perspective view of a component of one embodiment of a spinal implant system in accordance with the principles of the present disclosure.

Body 402 includes a surface 420 that defines a passageway 422. Passageway 422 has an oblong configuration and extends through body 402. In some embodiments, passageway 422 may have alternate cross section configurations, such as, for example, oval, cylindrical, triangular, square, polygonal, irregular, uniform, non-uniform, offset, staggered, undulating, arcuate, variable and/or tapered. Passageway 422 is configured for disposal of a spinal rod 450 such that connector 400 can be mounted with spinal rod 450.

Figure 13:
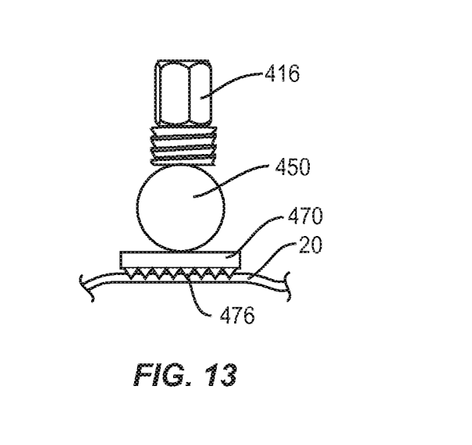
FIG. 13 is a side cross section view of components of one embodiment of a spinal implant system in accordance with the principles of the present disclosure.

In one embodiment, as shown in FIGS. 12 and 13, spinal implant system 10 includes an engaging member, such as, for example, a crown 470. Crown 470 includes a surface 472 and a surface 474. Surface 472 is configured for engagement with spinal rod 450. Surface 474 includes a plurality of gripping elements, such as, for example, projections 476 configured for engagement with tether 20. Projections 476 are configured to compress and penetrate the surface of tether 20 to fix tether 20 with connector 400.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a first portion;
   a second portion defining a longitudinal axis and being configured to penetrate tissue; and
   a tether having a section positioned within the first portion such that the section is coaxial with the longitudinal axis and a spinal implant connected with the tether is movable to a plurality of orientations relative to the longitudinal axis,
   wherein the first portion defines a cavity having the section disposed therein, the first portion comprising a wall circumferentially disposed about the cavity, the tether extending through the cavity.

2. A spinal construct as recited in claim 1, wherein the plurality of orientations includes a plurality of axes and/or a plurality of planes.

3. A construct as recited in claim 1, wherein the spinal implant is adjustable in a plurality of planes relative to the second portion.

4. A spinal construct as recited in claim 1, wherein the cavity extends past an uppermost surface of the wall.

5. A spinal construct as recited in claim 1, wherein the first portion includes an inner surface that defines the cavity, the inner surface being mechanically coupled to the section.

6. A spinal construct as recited in claim 1, wherein the first portion is swaged to the section.

7. A spinal construct as recited in claim 1, further comprising the spinal implant, wherein the spinal implant comprises a ring defining an opening, the tether being positioned within the opening.

8. A spinal construct as recited in claim 1, wherein an outer surface of the section includes adhesive material to fix the section to the first portion.

9. A spinal construct as recited in claim 1, wherein the first portion engages the section in a friction fit.

10. A spinal construct as recited in claim 1, wherein the first portion engages the section in a pressure fit.

11. A spinal construct as recited in claim 1, wherein an outer surface of the wall has a hexalobe geometry.

12. A spinal construct as recited in claim 1, wherein the tether is resorbable.

13. A spinal construct as recited in claim 1, wherein the tether is degradable.

14. A spinal construct comprising:
   a bone fastener comprising a head including an inner surface that defines a cavity, and a shaft defining a longitudinal axis and being configured to penetrate tissue; and
   a tether extending between a first end and a second end, the first end including a section that is positioned within the cavity such that the section is coaxial with the longitudinal axis and a spinal implant connected with the tether is movable to a plurality of orientations relative to the longitudinal axis,
   wherein the first portion defines a cavity having the section disposed therein, the first portion comprising a wall circumferentially disposed about the cavity.

15. A spinal construct as recited in claim 14, wherein an outer surface of the section includes adhesive material to fix the section to the head.

16. A spinal construct as recited in claim 14, wherein the head engages the section in a friction fit.

17. A spinal construct as recited in claim 14, wherein the head engages the section in a pressure fit.

18. A spinal construct comprising:
   a first portion;
   a second portion defining a longitudinal axis and being configured to penetrate tissue; and
   a tether fastened with the first portion such that a spinal implant connected with the tether is movable to a plurality of orientations relative to the longitudinal axis,
   wherein the first portion defines a circular cavity having the section disposed therein, the first portion comprising a wall circumferentially disposed about the cavity, the extending through an uppermost surface of the first portion, an outer surface of the wall having a hexalobe geometry configured for engagement with a similarly shaped tool.

* * * * *

UNITED STATES PATENT AND TRADEMARK OFFICE
CERTIFICATE OF CORRECTION

PATENT NO. : 9,848,919 B2
APPLICATION NO. : 14/704156
DATED : December 26, 2017
INVENTOR(S) : Simpson et al.

Page 1 of 1

It is certified that error appears in the above-identified patent and that said Letters Patent is hereby corrected as shown below:

In the Specification

In Column 2, Line 67, delete "for form" and insert -- to form --, therefor.

In Column 5, Line 15, delete "(TOP)," and insert -- (TCP), --, therefor.

In Column 5, Line 29, delete "dements" and insert -- elements --, therefor.

In Column 8, Line 49, delete "dosed." and insert -- closed. --, therefor.

In the Claims

In Column 11, Line 44, in Claim 3, delete "construct" and insert -- spinal construct --, therefor.

In Column 12, Line 48, in Claim 18, delete "the extending" and insert -- the tether extending --, therefor.

Signed and Sealed this
Twelfth Day of June, 2018

Andrei Iancu
*Director of the United States Patent and Trademark Office*